United States Patent [19]

Kohler

[11] 4,365,521
[45] Dec. 28, 1982

[54] DEVICE FOR THE FINE ADJUSTMENT IN ALL THREE DIRECTIONS OF SPACE OF AN INSTRUMENT ARRANGED ON A BASE

[75] Inventor: Kurt Kohler, Konigsbronn, Fed. Rep. of Germany

[73] Assignee: Carl Zeiss-Stiftung, Oberkochen, Fed. Rep. of Germany

[21] Appl. No.: 197,983

[22] PCT Filed: Jan. 10, 1980

[86] PCT No.: PCT/DE80/00001
 § 371 Date: Oct. 23, 1980
 § 102(e) Date: Oct. 6, 1980

[87] PCT Pub. No.: WO80/01751
 PCT Pub. Date: Sep. 4, 1980

[30] Foreign Application Priority Data

Feb. 23, 1979 [DE] Fed. Rep. of Germany ....... 2907099

[51] Int. Cl.³ .......................... G05G 7/00; A61B 3/12
[52] U.S. Cl. .................. 74/471 XY; 351/242
[58] Field of Search ...................... 74/471 XY; 351/35

[56] References Cited

U.S. PATENT DOCUMENTS 2,940,357 6/1960 Oswold .................................. 351/38
3,086,743 4/1963 Littmann ............................. 248/405
3,463,579 8/1969 Papritz ................................. 351/38
3,937,099 2/1976 Koehler ......................... 74/471 XY

FOREIGN PATENT DOCUMENTS 2907099 11/1980 Fed. Rep. of Germany .
 658932 7/1961 Italy ........................................ 351/38
 275858 6/1951 Switzerland .......................... 351/38
 499112 1/1939 United Kingdom .................. 351/38
 134897 5/1960 U.S.S.R. ................................. 351/38

Primary Examiner—Allan D. Herrmann

[57] ABSTRACT

A device for the fine adjustment in all three directions in space of an instrument arranged on a base by means of an actuating member. The actuating member consists of a handle the turning of which acts, via a universal joint, on the parts of the base adapted to provide vertical displacement of the instrument, and of an inner lever which when moved around the pivot point defined by the universal joint effects the horizontal displacement of the instrument with respect to a base plate. The inner lever is swingable towards all sides in a sleeve firmly connected with the base and its lower end is adapted with a ball foot which rests directly on the base plate. The bearing sleeve of the inner lever is arranged in or near the plane of the cardan joint; the radius of the ball foot corresponds to the distance between the bearing sleeve and the base plate.

5 Claims, 2 Drawing Figures

DEVICE FOR THE FINE ADJUSTMENT IN ALL THREE DIRECTIONS OF SPACE OF AN INSTRUMENT ARRANGED ON A BASE

The present invention relates to a device for the fine adjustment in all three directions in space of an instrument arranged on a base by means of an actuating member which can be swung to all sides for horizontal adjustment and rotated for vertical adjustment.

One such device is known (German Utility Model 18 18 245) in which the actuating member consists of a shaft which is rotatable for the vertical displacement of the instrument and is surrounded by a hollow handle. This handle is directly connected to a ball which is adapted to swing to all sides in the base of the instrument and via which the base rests on a support. Upon the swinging of the handle, the ball rolls on the base and thereby effects a horizontal displacement of the base. The shaft contained in the handle is turned via a turn knob which can be grasped together with the handle in one hand and transmits movement via a universal joint arranged in the ball to a spindle which vertically displaces the instrument.

This known device has the disadvantage that in any position of swing of the handle an unintended turning of the handle will effect a horizontal displacement of the base. Such unintentional turning is possible and cannot be prevented since the ball has a recess which, in every position of swing of the handle, permits the transfer of the rotation of the shaft to the spindle for displacement.

A solution is also known (German Patent No. 24 07 174) which improves the above-described device in such a manner that unintended horizontal displacement of the base is avoided. This device consists of a handle whose lower end is connected, via a universal joint, with a turnable portion of the base which is adapted to vertically adjust the instrument. This handle has an inner lever which, is coupled without play to the handle so that upon the swinging of handle around the pivot point defined by the universal joint, serves via a special support solely for the horizontal displacement of the base with respect to the base plate. The lower end of this inner lever engages a portion of the base of the instrument which lies on the base plate so that the turning of the lever does not result in an unintentional horizontal displacement of the base. This solution has the disadvantage that the base of the instrument rests flat on the part lying on the base plate and must be displaced with respect to said part for horizontal displacement. Since the friction between two surfaces must be overcome for adjustment, the forces to be expended are dependent on the load. A completely smooth displacement is possible only in case of a very accurately developed bearing surface. Such a bearing is expensive and is sensitive to the accumulation of dirt.

The same disadvantage is present in another known fine-adjustment device (German Pat. No. 12 63 347) in which a single-piece lever is provided for both the horizontal displacement and the vertical displacement. The lever is swingable to all sides in a single support place and is coupled with respect to its rotation to the support place. The lower end of this lever, in order to avoid unintended horizontal displacements upon turning of the lever, engages a part which rests on the base plate and against which the base of the instrument rests via a large surface. In this way the above-described disadvantages of a bearing surface arise.

The object of the present invention is to provide a device for the fine adjustment in all three directions in space of an instrument by means of one actuating member. It is a further object of the invention to provide a device which permits load-independent horizontal displacements which are substantially independent of dirt and/or wear of the bearing, and which is completely uncoupled from the vertical adjustment movement of the actuating member.

Starting from the known device with handle and inner lever, this objective is achieved in the manner that the lower end of the inner lever is developed as a ball foot which rests directly on the base plate and the radius of which corresponds to the distance between the pivot point of the handle and the base plate. The inner lever is supported in a manner swingable towards all sides but not turnable about its axis, in a sleeve which is firmly connected to the base of the instrument.

In accordance with the invention, therefore, upon the swinging of the actuating handle the lower end of the inner lever rolls on the base plate and thereby, via its support in the instrument base, displaces said base horizontally. This rolling movement is independent of the weight of the instrument arranged on the base and is substantially independent of dirt and/or wear of the ball foot of the inner lever. The vertical displacement of the instrument is effected by the turning of the actuating handle around its axis via a separate support. Since the inner lever is supported swingably but not turnably in the instrument base, it does not participate in such a rotation of the actuating handle so that an unintended horizontal displacement of the base is avoided in every position of swing of the handle.

In order to obtain the greatest possible range of swing of the handle it is advisable to arrange the support of the inner lever in the instrument base in or close to the plane of the universal joint. In this way, upon movement of the handle, the axis of the inner lever remains in the axis of the handle. In principle, it is also possible to arrange the support of the inner lever outside and preferably below the plane of the universal joint and in this way provide a stepdown between the swinging movement of the handle and the horizontal movement of the instrument base.

Since a turning of the handle does not require any great force, it is possible that, upon purely horizontal displacement, i.e. upon the swinging of the handle, a turning and thus a slight vertical displacement of the instrument will unintentionally take place. In order to exlude this source of error, it is advisable that the two parts of the actuating member are coupled for swinging but uncoupled for rotation; the upper part of the actuating handle being firmly connected with the upper end of the inner lever and the lower part being developed as turnable handle. For very precise adjustments, the observer applies his hand from above onto the actuating member and grasps the lower part with the fingers of that hand. Horizontal adjustment is effected by pure swinging of the actuating member which is conveniently effected via the upper part thereof. For the vertical displacement the lower part of the actuating member is then intentionally turned.

It should be expressly emphasized that with an actuating member developed in this manner, one-hand operation of the adjustment device is possible in connection with which any unintended displacement in horizontal or vertical direction can be avoided.

The invention will be explained in further detail below with reference to FIGS. 1 to 4 of the accompanying drawings, in which.

Figure 1:
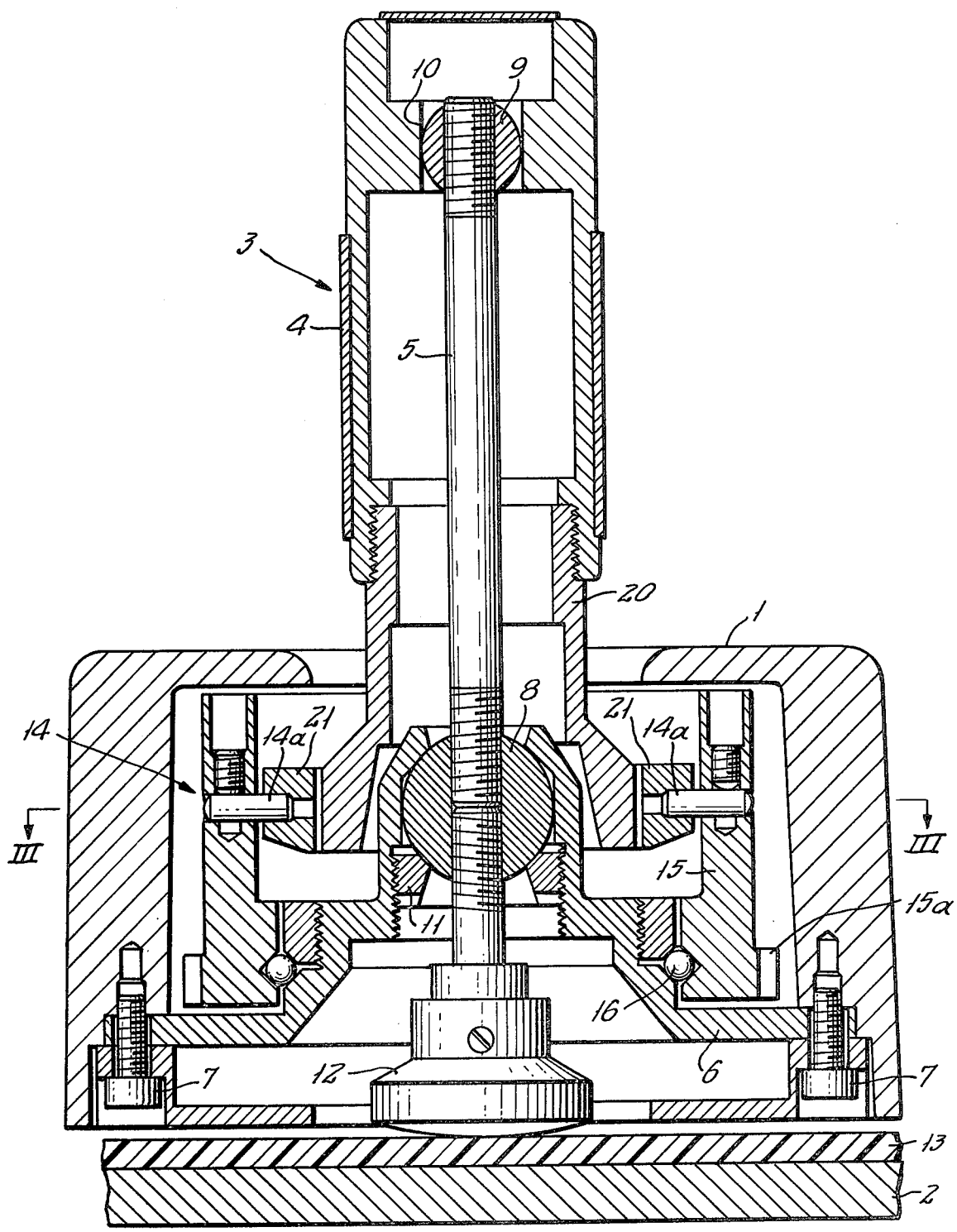
FIG. 1 is a section through one illustrative embodiment of an instrument base developed in accordance with the invention, seen in front view.

In FIG. 1, 1 is an instrument base which is arranged displaceably on a base plate 2. Base 1 bears an instrument, for instance an ophthalmological instrument, which is to be displaced horizontally and vertically. For such displacement in all three directions in space there is provided an actuating member 3 which consists of a handle 4 and an inner lever 5 arranged in said handle.

Within the instrument base 1 there is provided a sleeve 6 which is firmly connected by screws 7 with base 1. The upper part of the sleeve 6 is a support which receives a spherical thickening 8 firmly connected with inner lever 5. At its upper end lever 5 is provided with another spherical thickening 9 which is supported in a sleeve 10 of the handle 4. The part 10 is so tightened in the sleeve 6 that the thickening 8 of the lever 5 is swingable towards all sides in the sleeve 6. Since the friction between the thickening 8 and the sleeve 6 is set substantially higher than the friction between the upper thickening 9 and the sleeve 10, the lever 5 does not also turn upon the rotation of the handle 4.

The lower end of the lever 5 is developed as a ball foot 12 which rests directly on a plastic or rubber covering 13 of the base plate 12. Upon a swinging of the lever 5, the spherical head 12 rolls on the base 13. In this connection, the instrument base 1 is displaced horizontally with respect to the base plate 2 via the sleeve 6.

The inner lever 5 is surrounded by the handle 4 whose lower end is supported via a universal joint, designated schematically as 14, in a manner swingable towards all sides, in a cylindrical structural part 15. The part 15 rests via a ball bearing 16 against the sleeve 6 and is turnable around said sleeve. Such rotation is effected by turning the handle 4. This rotation is transmitted via the universal joint 14 to the structural part 15. A gear rim 15a connected with said part engages other transmission elements (not visible here) which finally, upon rotation of a part 15, effect a vertical displacement of the instrument on the base 1.

Figure 4:
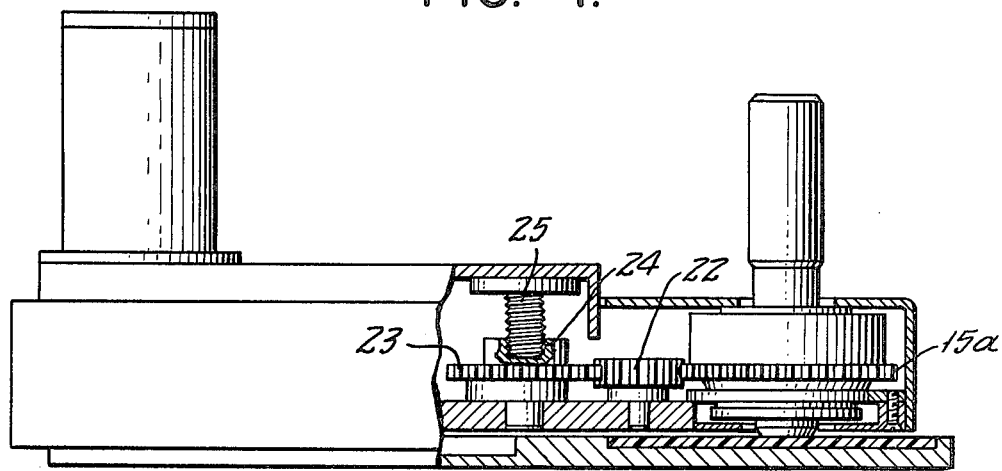
FIG. 4 is a side view of the device having a section of the housing cut-away.

As would be understood by one skilled in the art the above mentioned transmissional elements may take various forms. For example, gear rim 15a may be adapted with a gear belt or pulley which would transmit the rotational movement of rim 15a to a means to effect vertical displacement. In this regard, attention is directed to FIG. 4 wherein a gearing arrangement for effecting vertical movement of the instrument base is shown. Specifically rim gear 15a engages gear 22 which in turn transmits rotation to gear wheel 23 which is combined with a tubular sleeve 24. This sleeve is provided with an inside thread within which a vertical threaded spindle 25 is mounted so that rotation of gear wheel 23 causes vertical movement of said spindle. The spindle 25 presses against the instrument base 1 so that vertical movement of the spindle displaces the instrument base in a vertical direction.

For the adjustment of the instrument therefore observer grips the handle 4. Upon swinging around the pivot point defined by universal joint 14 ball foot 12 rolls on base 13 and, via support point of the inner lever 5 in sleeve 6, displaces the instrument base horizontally. Specifically, ring 21 is pivotally connected to member 15 by axes 14a. When swivelling lever 3 in a plane perpendicular to the plane of the paper, ring 21, together with sleeve 20, rotates about said axes 14a, while part 15 remains fixed. Similarly sleeve 20 is pivotally connected with ring 21 by a second pair of axes 14b which are arranged perpendicular to the plane of the paper, therefore when swivelling lever 3 in a direction which is in the plane of the paper, sleeve 20 rotates about these two axes while ring 21, together with the cylindrical part 15, remain fixed. Upon turning of the handle 4, the inner lever remains completely unaffected. The structural part 15 is also turned by handle 4 via universal joint 14. In this way the instrument is displaced vertically.

In FIG. 1, the pivot point of lever thickening 8 within sleeve 6 coincides with the pivot point of actuating member 3 which is defined by universal joint 14. The lower surface of ball foot 12 is spherical and its radius corresponds to the distance between the pivot point of actuating member 3 and base 13.

It is structurally not necessary for the pivot point of thickening 8 of the lever to coincide with the pivot point of actuating member 3 defined by universal joint 14. If they differ, however, the range of swing of actuating member 3 is limited by the fact that, with large angles of swing, inner lever 5 comes to rest against the inner surface of handle 4.

Figure 2:
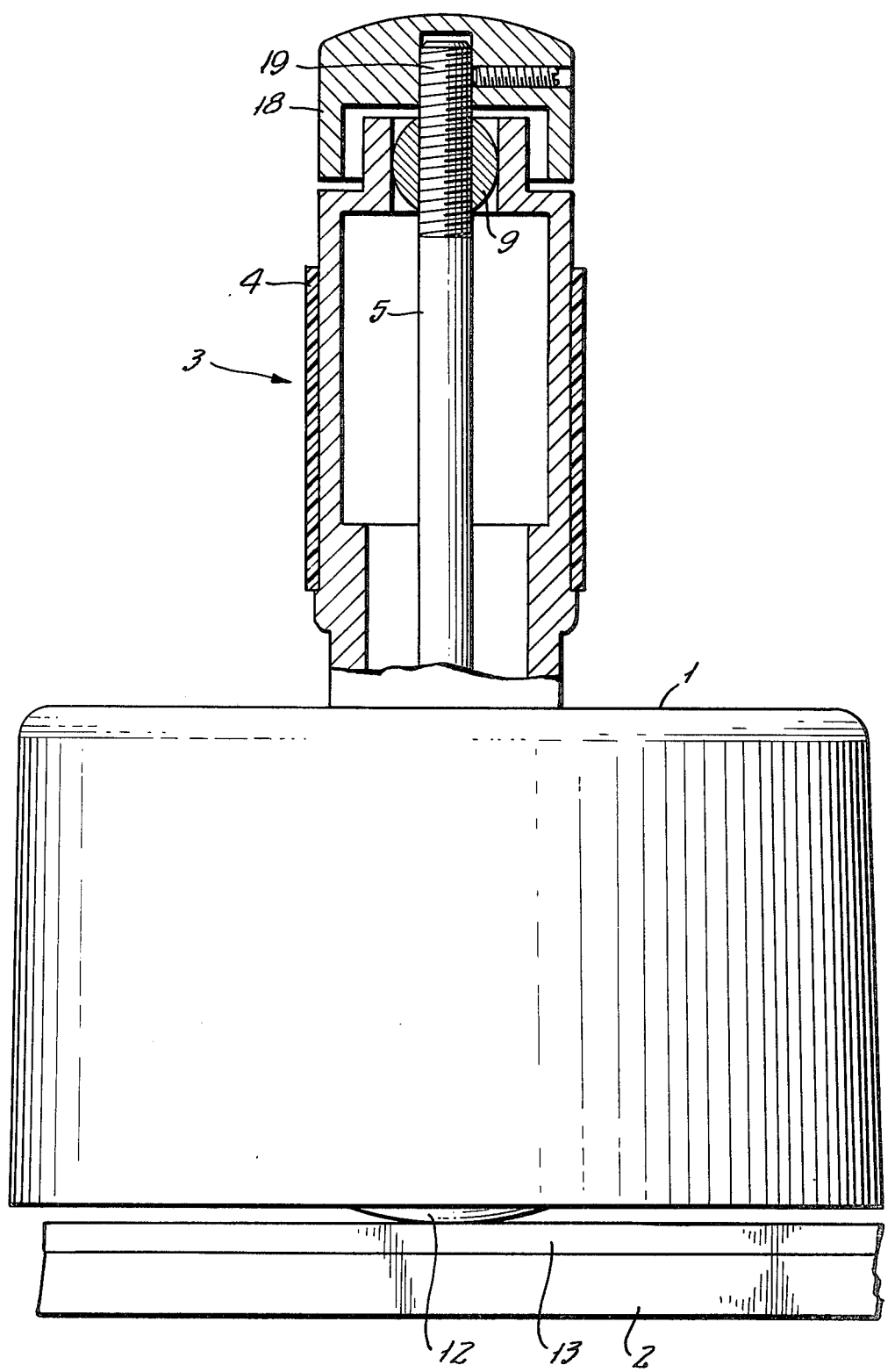
FIG. 2 is a cross section through an illustrative embodiment of an instrument base having a two-piece actuating member.
Figure 3:
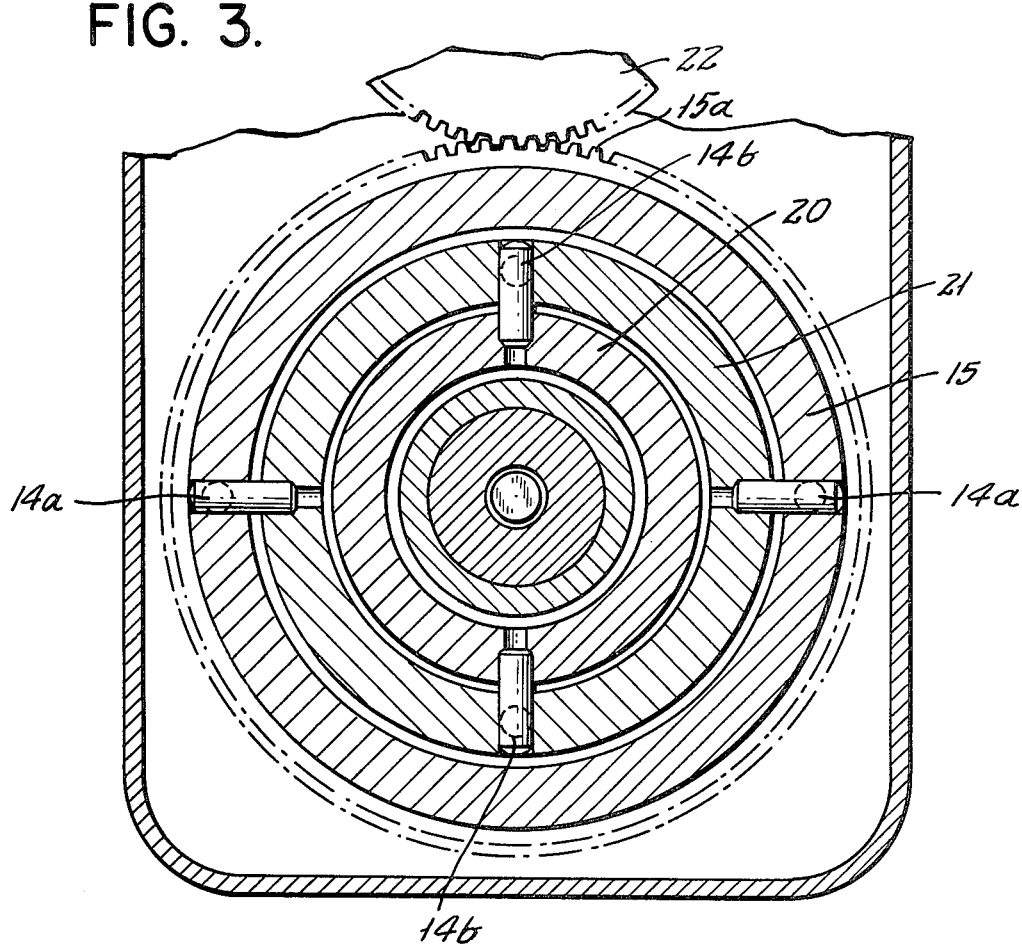
FIG. 3 is a partial, enlarged section taken on line III—III of FIG. 1.

In the embodiment shown in FIG. 1, the horizontal displacement is completely disconnected from the vertical displacement. It is, however, possible that the observer, upon swinging handle 4, may unintentionally turn it and thus produce an undesired vertical displacement of the instrument. Here the embodiment shown in FIG. 2 provides a remedy.

In this embodiment, structural part 18 is firmly connected with upper end 19 of extended inner lever 5. In this way structural part 18 is coupled with respect to swinging movement to handle 4 but disconnected from it with respect to the turning of handle 4.

In order to effect a very precise adjustment of the instrument, the observer places his hand from above on actuating member 3. His hand thus rests on part 18 and his fingers grasp handle 4. For the horizontal displacement a swinging of actuating member 3 is merely effected via part 18, in which case handle 4 cannot unintentionally be turned. For the vertical displacement the handle is intentionally turned.

It is, of course, possible to impart to actuating member 3, shown diagrammatically, a special development in the region of turnable handle 4 in order to permit optimal operation.

I claim:

1. A device for the fine adjustment of an instrument base in all directions of space, said adjustment being effected by an actuating member adapted to swing sideways for horizontal adjustment and rotatable about its vertical axis for vertical adjustment of said base, said actuating member comprising an outer rotatable handle connected via a universal joint to a rotatable member for effecting vertical displacement of the instrument base, said actuating member further comprising an inner lever provided at its lower end portion with a ball foot which contacts a base plate, the radius of said ball foot being equal to the distance between the pivot point of the handle and the base plate, said inner lever being supported by a lower support sleeve fixably attached to the instrument base and adapted to non-rotatably support said inner lever while allowing said lever to swing horizontally in all directions.

2. A device according to claim 1, wherein the lower portion of the inner lever is provided with a first spherical thickening which is frictionally engaged and supported by said lower support sleeve.

3. A device according to claim 2 in which the upper end of the inner lever is provided with a second spherical thickening which is frictionally engaged and supported in an upper support sleeve located in the handle, said second thickening and said upper support sleeve cooperating to rotatably support said handle on the inner lever, wherein the friction between the first spherical thickening and the lower sleeve is greater than the friction between the second spherical thickening and the upper support sleeve.

4. A device according to claims 1 or 2, wherein the first spherical thickening of the inner lever is arranged in close proximity to the plane of the universal joint.

5. A device according to claim 1, wherein the upper end portion of the inner lever extends beyond the outer rotatable handle and is provided with a knob member which is rotatably uncoupled from said outer handle.

* * * * *